United States Patent
Tsukagoshi et al.

(10) Patent No.: US 9,134,235 B2
(45) Date of Patent: Sep. 15, 2015

(54) SPFS SENSOR EQUIPPED WITH MECHANISM PURIFYING NON-SPECIFICALLY ADSORPTIVE CONTAMINANTS

(75) Inventors: Masanori Tsukagoshi, Hachioji (JP); Takatoshi Kaya, Inagi (JP); Noriaki Yamamoto, Machida (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 13/817,356

(22) PCT Filed: Jul. 27, 2011

(86) PCT No.: PCT/JP2011/067085
§ 371 (c)(1),
(2), (4) Date: Feb. 15, 2013

(87) PCT Pub. No.: WO2012/023391
PCT Pub. Date: Feb. 23, 2012

(65) Prior Publication Data
US 2013/0143332 A1  Jun. 6, 2013

(30) Foreign Application Priority Data

Aug. 17, 2010 (JP) ................................. 2010-182342

(51) Int. Cl.
*G01N 21/64* (2006.01)
*G01N 21/05* (2006.01)
*G01N 33/543* (2006.01)

(52) U.S. Cl.
CPC ............ *G01N 21/6402* (2013.01); *G01N 21/05* (2013.01); *G01N 21/648* (2013.01); *G01N 33/54373* (2013.01); *G01N 33/54393* (2013.01)

(58) Field of Classification Search
CPC . G01N 33/53; G01N 33/5306; G01N 33/543; G01N 33/54353; G01N 33/54366; G01N 33/54373; G01N 21/64; G01N 21/648
See application file for complete search history.

(56) References Cited

U.S. PATENT DOCUMENTS

| 5,135,717 A | 8/1992 | Renzoni et al. |
| 5,556,959 A | 9/1996 | Brush et al. |
| 5,808,044 A | 9/1998 | Brush et al. |

(Continued)

FOREIGN PATENT DOCUMENTS

| JP | 2006-105677 A | 4/2006 |
| JP | 2006-266742 A | 10/2006 |

(Continued)

OTHER PUBLICATIONS

Fang Yu et al. Surface Plasmon Fluorescence Immunoassay of Free Prostate-Specific Antigen in Human Plasma at the Femtomolar Level, Anal. Chem., 2004, 76 (22), pp. 6765-6770.

(Continued)

*Primary Examiner* — Melanie Y Brown
*Assistant Examiner* — Rebecca Martinez
(74) *Attorney, Agent, or Firm* — Cantor Colburn LLP (57) ABSTRACT

[Object] It is an object of the invention to provide a sensor area which can suppress a decrease in assay signal and an increase in assay blank in an SPFS measurement.
[Solution] An SPFS sensor chip of the invention includes a purification area and a sensor area arranged upstream and downstream, respectively, relative to each other along a flow direction in a channel for surface plasmon-field enhanced fluorescence spectroscopy [SPFS].

6 Claims, 6 Drawing Sheets

(56) References Cited

U.S. PATENT DOCUMENTS

| | | |
|---|---|---|
| 5,880,287 A | 3/1999 | Dandliker et al. |
| 5,994,063 A | 11/1999 | Metzker et al. |
| 6,221,604 B1 | 4/2001 | Upadhya et al. |
| 6,406,297 B1 | 6/2002 | Raymond et al. |
| 7,342,663 B2 | 3/2008 | Matsushita et al. |
| 2005/0042455 A1* | 2/2005 | Gedig et al. ............... 428/411.1 |
| 2007/0211254 A1* | 9/2007 | Matsushita et al. ........... 356/445 |
| 2009/0079978 A1 | 3/2009 | Kimura |
| 2009/0261269 A1 | 10/2009 | Horii et al. |
| 2009/0321662 A1* | 12/2009 | Ohtsuka ..................... 250/459.1 |
| 2010/0068824 A1 | 3/2010 | Kimura |

FOREIGN PATENT DOCUMENTS

| | | | |
|---|---|---|---|
| JP | 2007-24742 A | | 2/2007 |
| JP | 2010-71693 A | | 4/2010 |
| WO | 2005054826 A1 | | 6/2005 |
| WO | WO2008/052358 | * | 5/2008 |

OTHER PUBLICATIONS

International Search Report for International Application No. PCT/JP2011/067085, mailed Sep. 20, 2011, with English translation.

Written Opinion of the International Searching Authority, International Application No. PCT/JP2011/067085, mailed Sep. 20, 2011.

Extended European Search Report corresponding to Application No. 11818034.8-1554/2607888, PCT/JP2011067085; Date of Mailing: Jul. 20, 2015.

* cited by examiner

SPFS SENSOR EQUIPPED WITH MECHANISM PURIFYING NON-SPECIFICALLY ADSORPTIVE CONTAMINANTS

CROSS REFERENCE TO RELATED APPLICATIONS

This is the U.S. national stage of application No. PCT/JP2011/067085, filed on 27 Jul. 2011. Priority under 35 U.S.C. §119(a) and 35 U.S.C. §365(b) is claimed from Japanese Application No. 2010-182342, filed 17 Aug. 2010, the disclosure of which is also incorporated herein by reference.

TECHNICAL FIELD

The present invention relates to a combination of a purification area and a sensor area arranged in series in a channel for surface plasmon-field enhanced fluorescence spectroscopy [SPFS].

BACKGROUND ART

According to SPFS, a laser light is applied to the surface of a metal membrane under attenuated total reflection [ATR] conditions, and compressional waves (surface plasmons) are generated on the surface of the metal membrane in contact with a dielectric so as to increase the number of photons in the applied laser light several tens to several hundreds of times (the electric field enhancement effect by surface plasmons). In this manner, a fluorescent dye in the vicinity of the metal membrane is efficiently excited to allow for the detection of a trace amount and/or a trace concentration of an analyte.

Not only SPFS but other techniques for detecting a captured biomarker in a sample have a conventional problem in that contaminants in a sample such as blood or blood plasma inhibit the desired capturing reaction when the sample is brought into contact with a sensor area, resulting in a decrease in assay signal as well as an increase in assay blank. This problem is known to be mainly attributed to contaminants being non-specifically bound to a sensor substrate.

On the other hand, an increase in assay blank is caused also when the purity of a labeled antibody is not sufficiently high, as a result of labeled contaminants being captured by a sensor area.

Because SPFS is a system which detects a trace amount or a trace concentration as described above, there is an essential problem in that a decrease in assay signal and any increase in assay blank lead to a lowering in detection sensitivity. Further, the occurrence of any non-specific adsorption to such an extent that the resonance angle shifts causes a change in the degree of electric field enhancement in SPFS.

Patent Literature 1 discloses a biosensor for SPR measurement (SPR: surface plasmon resonance) that includes a substrate having at least a surface to which a bioactive substance has been bound and a surface (a reference section) free of bioactive substances, the reference section being protected with two or more kinds of hydrophilic groups in order to suppress non-specific adsorption to the reference section.

Patent Literature 2 discloses an SPR measurement sensor having, on the surface thereof, an active area in which ligands will be immobilized and a reference area free of the immobilization of ligands arranged in parallel to each other along the direction of an analyte flow. A difference is obtained between an active signal detected at the active area and a reference signal detected at the reference area, thereby cancelling an individual difference in measurement data between different sensors.

CITATION LIST

Patent Literatures

Patent Literature 1: JP-A-2006-266742
Patent Literature 2: JP-A-2006-105677

SUMMARY OF INVENTION

Technical Problem

Under the circumstances described above, it is considered very important also in SPFS to prevent non-specific adsorption onto a sensor area.

It is therefore an object of the invention to provide a sensor area which can be prevented from a decrease in assay signal and an increase in assay blank in an SPFS measurement.

Solution to Problem

The present inventors carried out studies in order to solve the problems described above. As a result, the present inventors have found that a non-specifically adsorptive component present in a sample can be removed beforehand by contacting the sample with a sample purification area before the contact with a sensor area. The present invention has been completed based on the finding.

That is, an SPFS sensor chip according to the present invention includes a purification area and a sensor area arranged upstream and downstream, respectively, relative to each other along a flow direction in a channel for surface plasmon-field enhanced fluorescence spectroscopy [SPFS].

The sensor area is preferably formed on a surface of a plasmon excitation sensor including a transparent support; a metal membrane formed on one surface of the support; a self-assembled monolayer [SAM] formed on the surface of the metal membrane opposite to the support; a hydrophilic polymer layer formed on the surface of the SAM opposite to the metal membrane; and a bioactive substance immobilized on the surface of the hydrophilic polymer layer opposite to the SAM.

The purification area preferably includes a sample purification area. The sample purification area is preferably formed on a surface of a sensor substrate including a transparent support; a metal membrane formed on one surface of the support; a self-assembled monolayer [SAM] formed on the surface of the metal membrane opposite to the support; and a hydrophilic polymer layer formed on the surface of the SAM opposite to the metal membrane.

More preferably, the purification area includes the sample purification area and a labeled antibody purification area, and the labeled antibody purification area is preferably formed on the surface of the plasmon excitation sensor.

It is preferable that a hydrophilic polymer forming the hydrophilic polymer layer in the sensor substrate, and a hydrophilic polymer forming the hydrophilic polymer layer in the plasmon excitation sensor be different from each other.

The purification area may be arranged in the entirety of a channel portion upstream from the sensor area.

An assay method according to the present invention includes at least the following steps (a) to (e):

Step (a): a step of bringing a sample into contact with the sample purification area;

Step (b): a step of bringing the sample having undergone the step (a) into contact with the sensor area;

Step (c): a step of reacting a conjugate of a ligand with a fluorescent dye with the sensor area having undergone the step (b), the ligand being the same or different from a ligand present in the plasmon excitation sensor;

Step (d): a step of applying a laser light to the plasmon excitation sensor having undergone the step (c) through the surface of the transparent support opposite to the metal membrane via a prism, and measuring the amount of fluorescence emitted from the excited fluorescent dye; and Step (e): a step of calculating the amount of an analyte contained in the sample based on the measurement results obtained in the step (d).

Preferably, the method further includes the following step (x):

Step (x): a step of bringing the conjugate into contact with the labeled antibody purification area beforehand.

Advantageous Effects of Invention

According to the present invention, a combination of the purification area and the sensor area can suppress a decrease in assay signal and an increase in assay blank in an SPFS measurement.

In the invention, a mixture of conjugates of a ligand or a contaminant with a fluorescent dye is purified so as to increase the purity of the conjugate of a ligand with a fluorescent dye. According to such an aspect, a combination of the purification area and the sensor area can further suppress a decrease in assay signal and an increase in assay blank.

BRIEF DESCRIPTION OF THE DRAWINGS

FIG. 3 depicts graphs which illustrate data of assay blank (the graph on the right) measured after a buffer and blood plasma were flowed through a channel as well as data (the graph on the left) obtained by converting the ratio of the signals into a ratio with respect to the signal for the buffer based on the above results. The measurement involved a substrate which included a transparent support, a metal membrane formed on one surface of the support and a self-assembled monolayer [SAM] formed on the surface of the metal membrane opposite to the support (this substrate corresponds to "SAM" in the graph), as well as a sensor substrate which further included a CMD [carboxymethyl dextran] layer formed on the surface of the SAM of the above substrate opposite to the metal membrane (this substrate corresponds to "CMD" in the graph). It is illustrated that the signals are lower and the assay blanks are higher in the case of blood plasma compared to the buffer (water-based).

DESCRIPTION OF EMBODIMENTS

Next, an SPFS sensor chip and an assay method using the chip according to the present invention will be described in detail.

(SPFS Sensor Chip)

An SPFS sensor chip according to the present invention includes a purification area and a sensor area arranged upstream and downstream, respectively, relative to each other along a flow direction in a channel for surface plasmon-field enhanced fluorescence spectroscopy [SPFS]. That is, the purification area and the sensor area in the SPFS sensor chip are arranged sequentially in series along a flow direction.

[Sensor Area]

Figure 1:
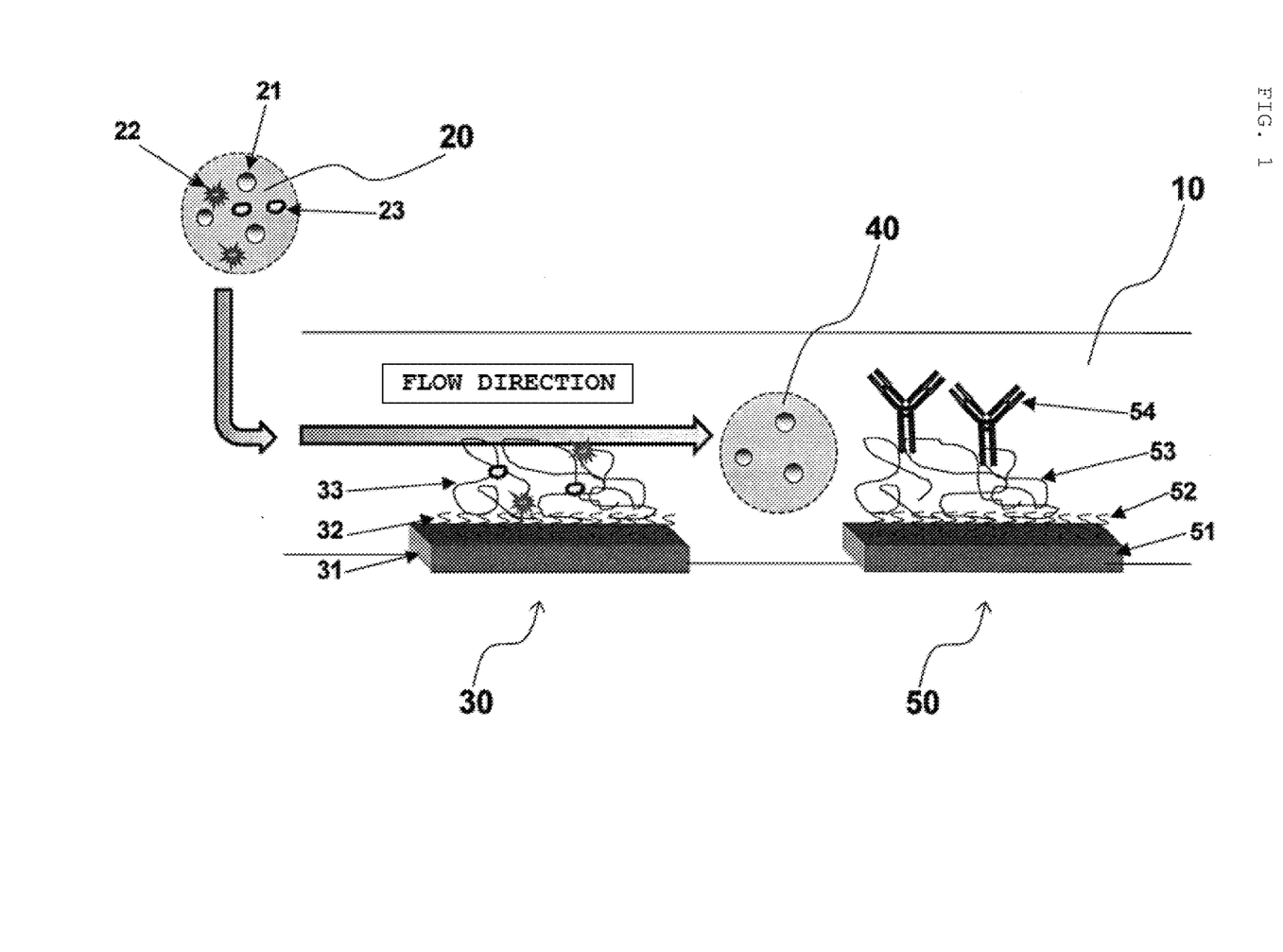
FIG. 1 is a schematic view depicting steps (a) and (b) in an inventive assay method, in which non-specifically adsorptive substances (22, 23) present in a sample (20) are removed by a sample purification area (30) arranged upstream along a flow direction in an SPFS channel (10), and the purified sample (40) (namely, the sample in which an analyte (21) is concentrated) is reacted with a sensor area (50).

The sensor area used in the invention is preferably formed on a surface of a plasmon excitation sensor including a transparent support; a metal membrane formed on one surface of the support; a self-assembled monolayer [SAM] formed on the surface of the metal membrane opposite to the support; a hydrophilic polymer layer formed on the surface of the SAM opposite to the metal membrane; and a bioactive substance immobilized on the surface of the hydrophilic polymer layer opposite to the SAM. In this area, as illustrated in FIG. 1, a purified sample (40), namely, a concentrated analyte is captured and subjected to an SPFS measurement.

(Transparent Support)

The "transparent support" used in the invention may be made of quartz, glass or a plastic such as a polycarbonate [PC] or a cycloolefin polymer [COP]. The refractive index [nd] is preferably 1.40 to 2.20, and the thickness is preferably 0.01 to 10 mm, and more preferably 0.5 to 5 mm. The size (length× width) is not particularly limited.

From the viewpoints of optical characteristics and cleaning properties, preferred commercial transparent glass substrates include "BK7" (refractive index [nd]: 1.52) and "LaSFN9" (refractive index [nd]: 1.85) manufactured by SCHOTT AG, "K-PSFn3" (refractive index [nd]: 1.84), "K-LaSFn17" (refractive index [nd]: 1.88) and "K-LaSFn22" (refractive index [nd]: 1.90) manufactured by SUMITA OPTICAL GLASS, Inc., and "S-LAL10" (refractive index [nd]: 1.72) manufactured by OHARA INC.

It is preferable that the surface of the transparent support be cleaned with an acid and/or plasma before a metal membrane is formed on the surface.

A preferred acid cleaning treatment is to soak the support in 0.001 to 1 N hydrochloric acid for 1 to 3 hours.

An exemplary plasma cleaning treatment is to soak the support in a plasma dry cleaner ("PDC 200" manufactured by YAMATO SCIENTIFIC CO., LTD.) for 0.1 to 30 minutes.

(Metal Membrane)

The "metal membrane" formed on one surface of the transparent support preferably includes at least one metal selected from the group consisting of gold, silver, aluminum, copper and platinum, and more preferably includes gold. An alloy of any of these metals is also usable. These metal species are preferable because they are stable to oxidation and the electric field enhancement by surface plasmons is large.

Only in the case where a flat glass plate is used as the transparent support, the transparent support is preferably coated with a membrane of chromium, nickel chromium alloy or titanium beforehand because such a coating provides stronger adhesion between the glass and the metal membrane.

For example, the metal membrane may be formed on the transparent support by methods such as sputtering methods, deposition methods (e.g., resistance heating deposition methods, electron beam deposition methods), electroplating and electroless plating methods. Because membrane production conditions are easily controllable, a sputtering method or a deposition method is preferably adopted in order to form a chromium membrane and/or the metal membrane.

The thickness of the metal membrane is preferably 5 to 500 nm for gold, 5 to 500 nm for silver, 5 to 500 nm for aluminum, 5 to 500 nm for copper, 5 to 500 nm for platinum, and 5 to 500 nm for an alloy of any of these metals. The thickness of the chromium membrane is preferably 1 to 20 nm.

From the viewpoint of electric field enhancement effect, the thickness is more preferably 20 to 70 nm for gold, 20 to 70 nm for silver, 10 to 50 nm for aluminum, 20 to 70 nm for copper, 20 to 70 nm for platinum, and 10 to 70 nm for an alloy of any of these metals, and the thickness of the chromium membrane is more preferably 1 to 3 nm.

The above thicknesses of the metal membranes are preferable because surface plasmons are generated easily. As long as the metal membrane has the above thickness, the size thereof (length×width) is not particularly limited.

(SAM)

SAM [self-assembled monolayer] is formed on the surface of the metal membrane opposite to the transparent support, and functions as a base for the immobilization of a bioactive substance, preferably a hydrophilic polymer to the metal membrane.

In the invention, the molecules forming this SAM are usually of a carboxyalkanethiol having about 4 to 20 carbon atoms (for example, available from DOJINDO LABORATORIES and Sigma-Aldrich Japan), and are particularly preferably of 10-carboxy-1-decanethiol. Carboxyalkanethiols with 4 to 20 carbon atoms are advantageous in that SAM formed of such molecules has little optical effects, namely, has such characteristics as high transparency, low refractive index and small layer thickness.

The SAM may be formed by any known method without limitation. For example, a method may be adopted in which a transparent glass support on which the metal membrane has been formed is soaked in an ethanol solution containing 10-carboxy-1-decanethiol (manufactured by DOJINDO LABORATORIES). As a result, the thiol group of 10-carboxy-1-decanethiol forms a bond with the metal and anchors the molecule. In this manner, the molecules are self-assembled on the surface of the metal membrane to form SAM.

(Hydrophilic Polymer Layer)

The hydrophilic polymer layer is preferably provided so as to mediate the bonding between the SAM and a bioactive substance. The hydrophilic polymer forming the hydrophilic polymer layer may be a polysaccharide, preferably a dextran such as carboxymethyl dextran [CMD], or a synthetic resin, preferably a polyacrylic acid.

For example, the hydrophilic polymer layer may be formed on the surface of the SAM by activating the carboxyl group of the hydrophilic polymer with a water-soluble carbodiimide, in detail 1-(3-dimethylaminopropyl)-3-ethylcarbodiimide [EDC], alone or a combination of EDC and N-hydroxysuccinimide [NHS], and then reacting the activated group with the amino group of the SAM. However, this method is illustrative and any of other known methods may be used appropriately in the invention.

(Bioactive Substance)

The bioactive substance may be a protein which specifically binds to a target substance. Examples thereof include antibodies specifically binding to antigens, with specific examples including enzymes to substrates/coenzymes, receptors to hormones, proteins A/proteins G to antibodies, avidins to biotin, and calmodulins to calcium. Of these, antibodies are preferred "proteins which specifically bind to a target substance".

The bioactive substance may be immobilized by any known method, for example by activating the carboxyl group of the SAM or the hydrophilic polymer with EDC alone or a combination of EDC and NHS, and then immobilizing the bioactive substance through its amino group. When a protein, which is a preferred bioactive substance, is used as the bioactive substance, the immobilization method is not limited to the above method as long as the protein is not deactivated.

[Purification Area]

The purification area preferably includes a sample purification area, and more preferably includes both a sample purification area and a labeled antibody purification area.

The purification area is preferably arranged in the entirety of a channel portion upstream from the sensor area.

[Sample Purification Area]

The sample purification area is an area which non-specifically adsorptive substances except an analyte, namely, contaminants present in the sample are non-specifically adsorbed and attached to. The sample having passed through this purification area is cleared of part (preferably all) of the contaminants.

Examples of the non-specifically adsorptive substances include albumins. Albumins are preferentially captured by the sample purification area.

The sample purification area is preferably formed on a surface of a sensor substrate including a transparent support; a metal membrane formed on one surface of the support; a self-assembled monolayer [SAM] formed on the surface of the metal membrane opposite to the support; and a hydrophilic polymer layer formed on the surface of the SAM opposite to the metal membrane.

That is, the "sensor substrate" (the sample purification area) has the same configuration as the "plasmon excitation sensor" (the sensor area) except that no bioactive substances are immobilized to the hydrophilic polymer layer. The sensor substrate may be fabricated by the same method as producing the plasmon excitation sensor except that no bioactive substances are immobilized.

A hydrophilic polymer forming the hydrophilic polymer layer in the "plasmon excitation sensor" (the sensor area and the labeled antibody purification area) may be different from or the same as a hydrophilic polymer forming the hydrophilic polymer layer in the "sensor substrate" (the sample purification area). It is preferable that these hydrophilic polymers be different because a wider variety of contaminants present in the sample can be non-specifically adsorbed and attached to the polymers with the result that a decrease in assay signal and an increase in assay blank can be suppressed more effectively.

[Labeled Antibody Purification Area]

The labeled antibody purification area is an area which, from a mixture of conjugates of a ligand of an antibody or the like labeled with a fluorescent dye and of possible various trace contaminants (e.g., non-specifically adsorptive substances, and antibodies that do not recognize an analyte) labeled with a fluorescent dye, namely, a mixture of ligand/fluorescent dye conjugates and contaminant/fluorescent dye conjugates, the contaminant/fluorescent dye conjugates are non-specifically adsorbed and attached to. The mixture having passed through this purification area is cleared of part (preferably all) of the contaminant/fluorescent dye conjugates as a result of these conjugates having been adsorbed and attached mainly to the labeled antibody purification area.

Figure 2:
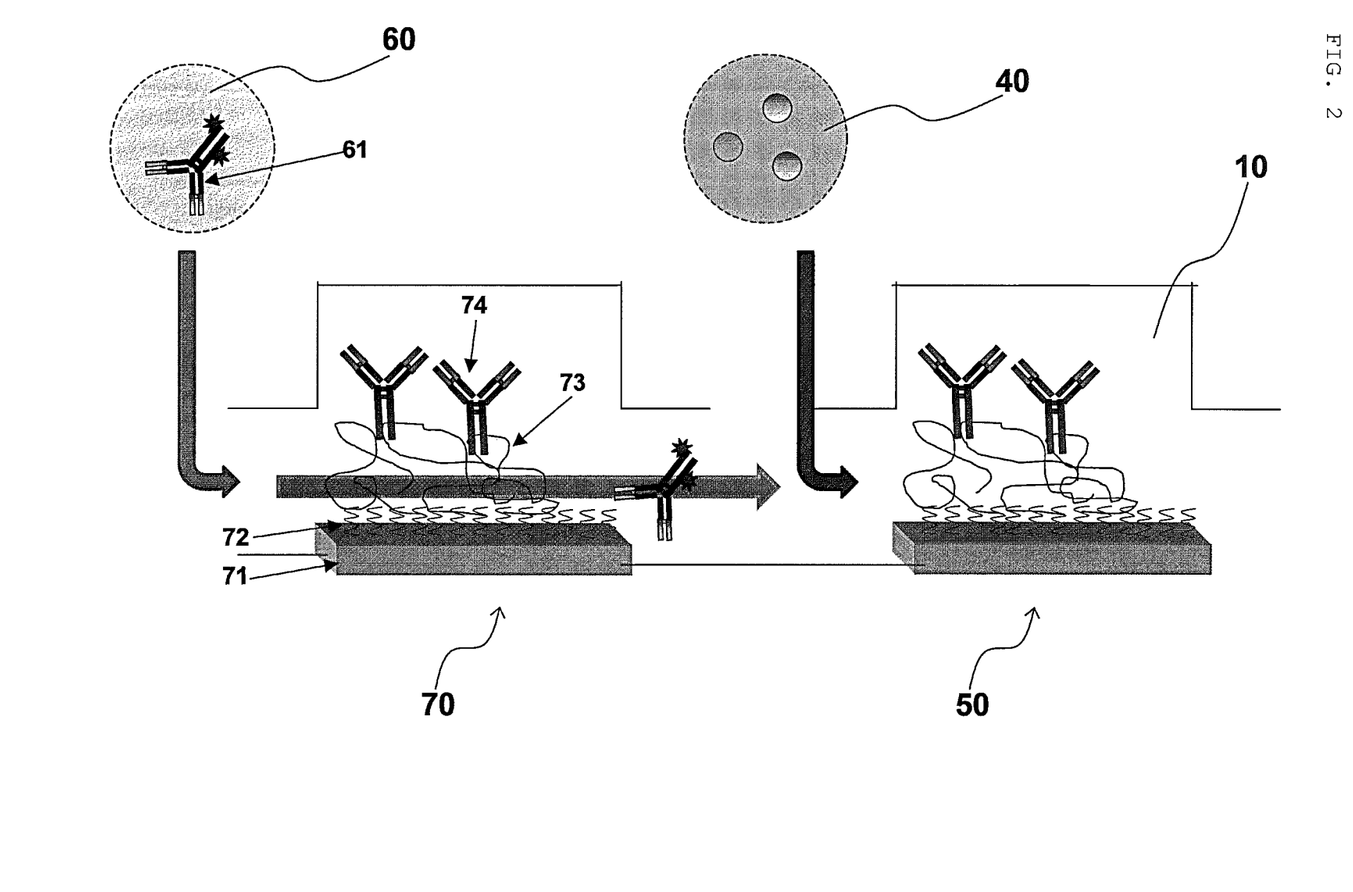
FIG. 2 is a schematic view depicting a step (x) preferably included in the inventive assay method, in which a labeled antibody liquid (60) is brought into contact with a labeled antibody purification area (70) in the SPFS channel (10) to remove a labeled contaminant (not shown) present in the labeled antibody liquid (60), and thereafter the purified sample (40) and labeled antibody (61) are subjected to a reaction in the sensor area (50).
Figure 3:
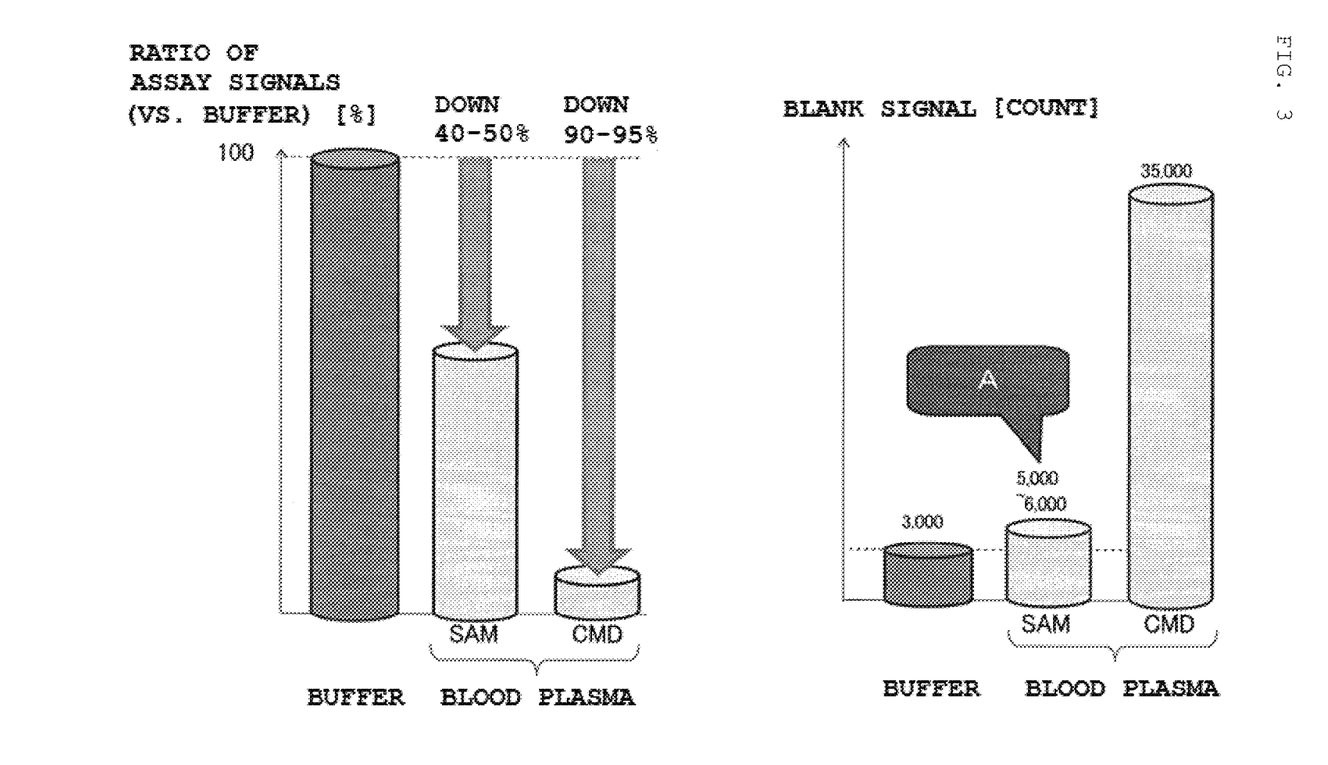
Figure 4:
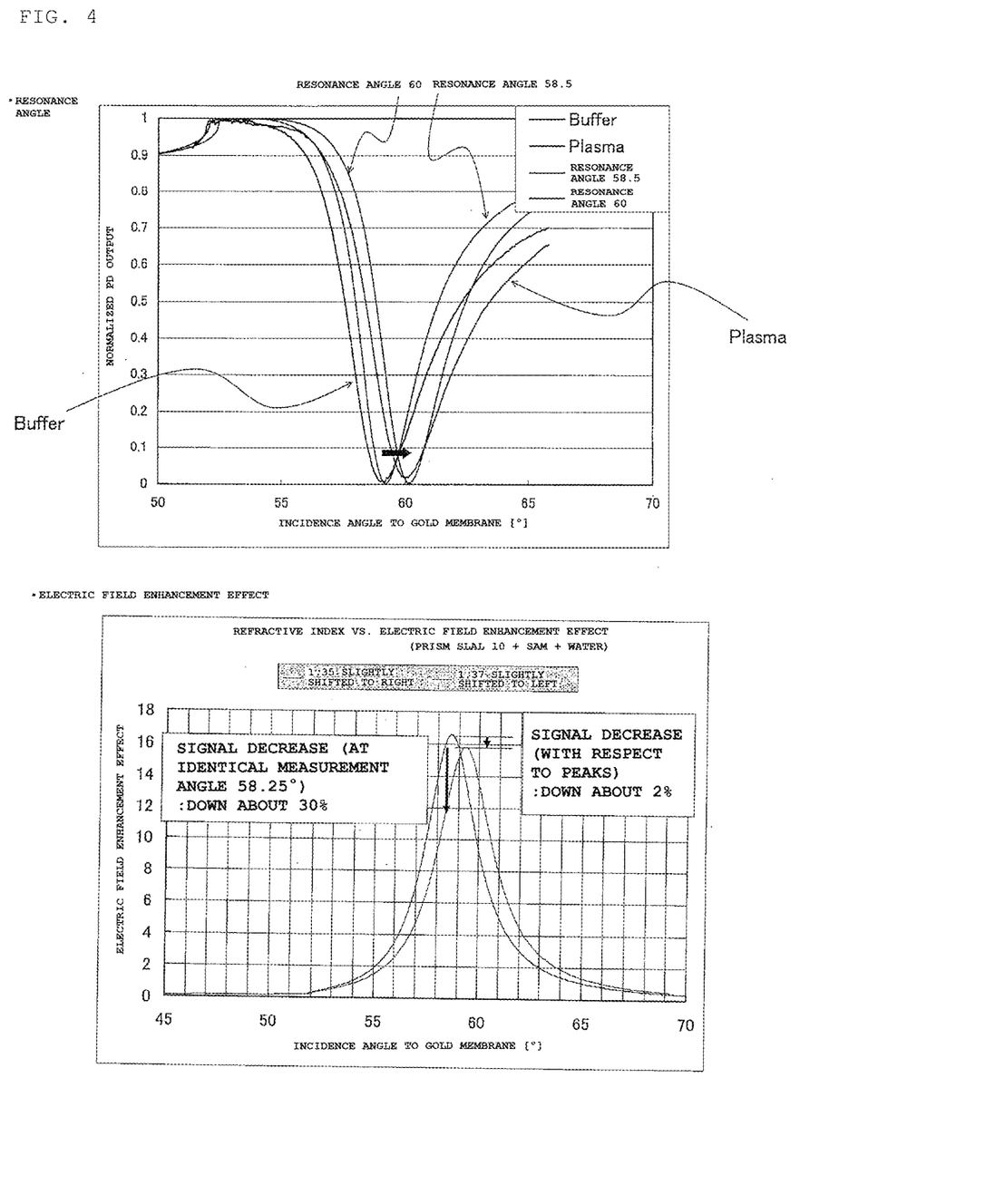
FIG. 4 depicts that flowing of blood plasma over the sensor substrate results in an approximately 1° shift of the resonance angle due to the adsorption of some components in the blood plasma onto the sensor substrate, relative to the resonance angle obtained when the buffer is flowed over the sensor substrate (the graph on the top), as well as that the signal in the former case is lowered by about 2% when the electric field enhancement effects are compared with respect to the respective peaks and by as much as about 30% when the electric field enhancement effects are compared with respect to an identical measurement angle (the graph on the bottom).

The labeled antibody purification area is preferably formed on the surface of the above "plasmon excitation sensor". That is, it is preferable that the labeled antibody purification area and the sensor area have the same configuration. When the labeled antibody purification area and the sensor area have the same configuration, as illustrated in FIG. 2, the labeled antibody liquid (60) is passed through the labeled antibody purification area (70) having the same configuration as the sensor area (50) and thereby part (preferably all) of contaminants, namely, labeled antibodies that do not bind to an analyte as well as non-specifically adsorptive substances are removed by being adsorbed and attached mainly to the labeled antibody purification area. Thus, advantageously, there remain almost no contaminants binding to components of the sensor area (50) with the result that a decrease in assay signal and an increase in assay blank can be suppressed more effectively.

In the above case, the labeled antibody purification area may be fabricated in the same manner as producing the sensor area.

When the labeled antibody purification area is used, the channel may be, for example, a Y-shaped channel (the sample purification area and the labeled antibody purification area define respective branches and merge with each other to lead to the sensor area) or a linear channel in which the sensor substrate (the sample purification area) is used first and, after being used, is removed from the channel and the plasmon excitation sensor (the labeled antibody purification area) is placed at the same location.

Further, it is preferable to adopt a configuration in which the sample having been passed through the sample purification area and the labeled antibody having been passed through the labeled antibody purification area are subjected to respective reactions in this sequence, namely, the purified sample is passed through the sensor area first and thereafter the purified labeled antibody is passed through the sensor area.

(Assay Method)

An assay method according to the present invention includes at least the following steps (a) to (e), and preferably includes a cleaning step and further the following step (x).

Step (a): a step of bringing a sample into contact with the sample purification area.

Step (b): a step of bringing the sample having undergone the step (a) into contact with the sensor area.

Step (c): a step of reacting a conjugate of a ligand with a fluorescent dye with the sensor area having undergone the step (b), the ligand being the same or different from a ligand in the plasmon excitation sensor.

Step (d): a step of applying a laser light to the plasmon excitation sensor having undergone the step (c) through the surface of the transparent support opposite to the metal membrane via a prism, and measuring the amount of fluorescence emitted from the excited fluorescent dye.

Step (e): a step of calculating the amount of an analyte contained in the sample based on the measurement results obtained in the step (d).

Cleaning step: a step of cleaning the surface of the plasmon excitation sensor having undergone the step (b) and/or the surface of the plasmon excitation sensor having undergone the step (c).

Step (x): a step of bringing the conjugate described above into contact with the labeled antibody purification area beforehand.

[Step (a)]

In the step (a), a sample is brought into contact with the sample purification area.

(Sample)

Examples of the "sample" include blood (blood serum, blood plasma), urine, nasal fluid, saliva, stool and body cavity fluids (such as spinal fluids, peritoneal fluids and pleural fluids). Prior to use, the sample may be appropriately diluted with a desired solvent, a buffer or the like. Of these samples, blood, blood serum, blood plasma, urine, nasal fluid and saliva are preferable.

(Contact)

The "contact" is preferably carried out in such a manner that the sample is carried by a carrier liquid circulating in the channel and is allowed to contact with the sample purification area while only the surface of the sensor substrate on the side of the hydrophilic polymer layer is soaked in the carrier liquid.

As described above, the "channel" is shaped like a rectangular tube or a round tube (pipe). The channel preferably has a rectangular structure in the vicinity of locations where the sensor substrate and the plasmon excitation sensor (hereinafter, these are collectively referred to as "chip") are placed, and a round tube (pipe) structure in the vicinity of a portion through which a drug solution is delivered.

Exemplary materials of chip portions and channel top panels include homopolymers and copolymers including monomers such as methyl methacrylate and styrene; and polyolefins such as polyethylene. Exemplary materials of drug solution delivery portions include silicone rubbers, Teflon (registered trademark) and polymers such as polyethylene and polypropylene.

In order to increase the efficiency of contact with the sample and to reduce the diffusion distance, it is preferable that the longitudinal and transverse cross sections of the channel in the chip portions be each independently about 100 nm to 1 mm.

In the case of small-scale lots (on a laboratory level), the chip is preferably fixed in the channel in such a manner that a polydimethylsiloxane [PDMS] sheet having a channel height of 0.5 mm is pressed against the surface of the chip on the metal membrane side so as to surround a portion of the chip where the metal membrane is formed, and thereafter the polydimethylsiloxane [PDMS] sheet and the chip are fixed together with a fastener such as a screw.

In the case of industrial large-scale lots (on a plant level), the chip may be fixed in the channel in such a manner that an integral plastic article with a substrate is provided or a separately-fabricated substrate is fixed to an integral plastic article, then the components such as the SAM and the hydrophilic polymer layer are formed on the surface of the metal membrane, and thereafter the channel is closed with a integral plastic article corresponding to a channel top panel. As required, a prism may be integrally formed with the channel.

The "carrier liquid" is preferably the same as the solvent or buffer used to dilute the sample. Examples include, although not particularly limited to, phosphate-buffered saline [PBS], Tris-buffered saline [TBS] and HEPES-buffered saline [HBS].

The carrier liquid may be circulated at a variable temperature for a variable time in accordance with the type of the sample without limitation. Usually, the temperature and the time are 20 to 40° C. and 1 to 60 minutes, and preferably 37° C. and 5 to 15 minutes.

The initial concentration of an analyte present in the sample being carried may be 100 µg/mL to 0.001 pg/mL.

The total volume of the carrier liquid, namely, the volume of the channel is usually 0.001 to 20 mL, and preferably 0.1 to 1 mL.

The flow rate of the carrier liquid is usually 1 to 2,000 µL/min, and preferably 5 to 500 µL/min.

[Step (b)]

In the step (b), the sample having undergone the step (a) is brought into contact with the sensor area. The sample obtained from the step (a) has a higher analyte concentration as a result of various contaminants having been non-specifically adsorbed and attached to the sample purification area (namely, the hydrophilic polymer layer, the SAM and the surface of the metal membrane of the sensor substrate).

(Contact)

The "contact" is preferably carried out in such a manner that the sample is carried by the carrier liquid circulating in the channel and is allowed to contact with the sensor area while only the surface of the plasmon excitation sensor on the side where a first ligand has been immobilized is soaked in the carrier liquid.

[Cleaning Step]

In the cleaning step, the surface of the plasmon excitation sensor having undergone the step (b) and/or the surface of the plasmon excitation sensor having undergone the step (c) is cleaned.

For example, a desired cleaning liquid for use in the cleaning step is a solution of a surfactant such as Tween 20 or Triton X100, the concentration being preferably 0.00001 to 1% by weight, or a salt such as sodium chloride or potassium chloride, the concentration being preferably 10 to 500 mM, in the same solvent or buffer as used in the reactions in the steps (b) and (c). Alternatively, the cleaning liquid may be a low-pH buffer, for example, 10 mM glycine HCl with a pH of 1.5 to 4.0.

The cleaning liquid is preferably circulated at the same temperature and flow rate as the temperature and flow rate for circulating the carrier liquid in the step (b).

The circulation time for the cleaning liquid is usually 0.5 to 180 minutes, and preferably 5 to 60 minutes.

[Step (c)]

In the step (c), a conjugate of a ligand (a second ligand), which may be the same or different from the ligand (the first ligand) in the plasmon excitation sensor, with a fluorescent dye is reacted with the sensor area having undergone the step (b), preferably having undergone the cleaning step.

(Fluorescent Dye)

In the present invention, the term "fluorescent dye" is a collective term for substances which emit fluorescence upon being irradiated with a specific excitation light or being excited by an electric field effect. The term "fluorescence" comprehends various kinds of light such as phosphorescence.

The fluorescent dye used in the present invention may be any of known fluorescent dyes without limitation as long as the emission from the fluorescent dye is not quenched due to the absorption of light by the metal membrane. It is usually preferable to use a fluorescent dye that allows the use of a fluorescence meter equipped with a filter rather than a monochromometer and has a large Stokes shift which increases detection efficiency.

Examples of the fluorescent dyes include fluorescent dyes of fluorescein family (manufactured by Integrated DNA Technologies Inc.), fluorescent dyes of polyhalofluorescein family (manufactured by Applied Biosystems Japan, Co., Ltd.), fluorescent dyes of hexachlorofluorescein family (manufactured by Applied Biosystems Japan, Co., Ltd.), fluorescent dyes of coumarin family (manufactured by Invitrogen Corporation), fluorescent dyes of Rhodamine family (manufactured by GE Healthcare Bioscience Corporation), fluorescent dyes of cyanine family, fluorescent dyes of indocarbocyanine family, fluorescent dyes of oxazine family, fluorescent dyes of thiazine family, fluorescent dyes of squaraine family, fluorescent dyes of chelated lanthanide family, fluorescent dyes of BODIPY (registered trademark) family (manufactured by Invitrogen Corporation), fluorescent dyes of naphthalenesulfonic acid family, fluorescent dyes of pyrene family, fluorescent dyes of triphenylmethane family, and Alexa Fluor (registered trademark) dye series (manufactured by Invitrogen Corporation). Further, fluorescent dyes described in U.S. Pat. No. 6,406,297, U.S. Pat. No. 6,221,604, U.S. Pat. No. 5,994,063, U.S. Pat. No. 5,808,044, U.S. Pat. No. 5,880,287, U.S. Pat. No. 5,556,959 and U.S. Pat. No. 5,135,717 may be used in the invention.

Table 1 describes the absorption wavelengths (nm) and the emission wavelengths (nm) of typical fluorescent dyes belonging to these families.

[Table 1]

TABLE 1

| Fluorescent dyes | Families | Absorption wavelengths (nm) | Emission wavelengths (nm) |
|---|---|---|---|
| Aminomethylcoumarin, AMCA | Coumarin | 350 | 450 |
| Cy2 (registered trademark) | Cyanine | 492 | 510 |
| Fluorescein Isothiocyanate, FITC | Fluorescein | 492 | 520 |
| Cy3 (registered trademark) | Indocarbocyanine | 550 | 570 |
| Tetramethyl Rhodamine Isothiocyanate, TRITC | Rhodamine | 550 | 570 |
| Rhodamine Red-X, RRX | | 570 | 590 |
| Texas Red, TR | | 596 | 620 |
| Cy5 (registered trademark) | Cyanine | 650 | 670 |
| Alexa Fluor (registered trademark) 647 | Cyanine | 650 | 665 |

The fluorescent dyes are not limited to the above organic fluorescent dyes. For example, a fluorescent dye including a complex of a rare earth such as Eu or Tb may also be used as the fluorescent dye in the invention. Rare earth complexes generally have a large difference in wavelength between the excitation wavelength (about 310 to 340 nm) and the emission wavelength (near 615 nm for a Eu complex, and near 545 nm for a Tb complex) and as long a fluorescence lifetime as several hundreds of microseconds or more. An example of commercially available fluorescent dyes of rare earth complexes is ATBTA-$Eu^{3+}$.

In performing the fluorescence assay according to the present invention described later, it is desirable to use a fluorescent dye having a maximum fluorescence wavelength in a wavelength region where the absorption of light by the metal contained in the metal membrane is small. In the case of gold as the metal membrane, it is desirable to use a fluorescent dye having a maximum fluorescence wavelength of not less than 600 nm in order to suppress the influence of the light absorption by the gold membrane to the minimum. Thus, in this case, it is particularly desirable to use a fluorescent dye having a maximum fluorescence wavelength in a near infrared region, with examples including Cy5 and Alexa Fluor (registered trademark) 647. Such a fluorescent dye having a maximum fluorescence wavelength in a near infrared region is useful even in the case where blood is used as the sample because the influence of the light absorption by iron derived from blood cell components in the blood can be suppressed to the minimum. In the case where silver is used as the metal membrane, it is desirable to use a fluorescent dye having a maximum fluorescence wavelength of not less than 400 nm.

The fluorescent dyes may be used singly, or two or more kinds may be used in combination.

(Conjugate of Second Ligand with Fluorescent Dye)

Regarding the "conjugate of a ligand (a second ligand), which may be the same or different from the ligand (the first ligand) in the sensor area, with a fluorescent dye used in the invention", the ligand, in the case where the ligand is a secondary antibody, is preferably an antibody which can recognize and bind to an analyte (a target antigen) contained in the sample.

In the assay method of the invention, the second ligand is used for the purpose of labeling an analyte with the fluorescent dye, and may be the same or different from the first ligand. In the case where a primary antibody used as the first ligand is a polyclonal antibody, a secondary antibody used as the second ligand may be a monoclonal antibody or a polyclonal antibody. However, in the case where the primary antibody is a monoclonal antibody, it is desirable that the secondary antibody be a monoclonal antibody recognizing an epitope which is not recognized by the primary antibody or be a polyclonal antibody.

In another preferred embodiment, a composite is used in which a secondary antibody has bound to a second analyte (a competitive antigen) which competes with an analyte (a target antigen) contained in the sample (wherein the competitive antigen is different from the target antigen). Such an embodiment is preferable because the amount of fluorescent signals (fluorescence signals) can be proportional to the amount of the target antigen.

In the case where a secondary antibody is used as the second ligand, the second ligand/fluorescent dye conjugate may be produced by any of methods including a method in which a carboxyl group is first introduced into a fluorescent dye and is converted into an active ester group with a water-soluble carbodiimide [WSC] (for example, 1-ethyl-3-(3-dimethylaminopropyl) carbodiimide hydrochloride [EDC]) and N-hydroxysuccinimide [NHS], and the active esterified carboxyl group is subjected to a dehydration reaction with the amino group of a secondary antibody with use of a water-soluble carbodiimide so as to effect immobilization; a method in which a secondary antibody and a fluorescent dye having an isothiocyanate and an amino group, respectively, are reacted with each other so as to effect immobilization; a method in which a secondary antibody and a fluorescent dye having a sulfonyl halide and an amino group, respectively, are reacted with each other so as to effect immobilization; a method in which a secondary antibody and a fluorescent dye having a iodoacetamide and a thiol group, respectively, are reacted with each other so as to effect immobilization; and a method in which a biotinylated fluorescent dye and a streptavidinated secondary antibody (or a streptavidinated fluorescent dye and a biotinylated secondary antibody) are reacted with each other so as to effect immobilization.

The concentration of the second ligand/fluorescent dye conjugate in the carrier liquid is preferably 0.001 to 10,000 μg/mL, and more preferably 1 to 1,000 μg/mL.

The carrier liquid may be circulated at the same temperature and the same flow rate for the same duration of time as described in the step (b).

[Step (x)]

In the step (x), the conjugate is brought into contact with the labeled antibody purification area beforehand. In the step (x), as illustrated in FIG. 2, the labeled antibody liquid (60) is brought into contact with the labeled antibody purification area (70) to remove labeled contaminants from the labeled antibody (60).

[Step (d)]

In the step (d), a laser light is applied to the plasmon excitation sensor having undergone the step (c), preferably having undergone the cleaning step, through the surface of the transparent support opposite to the metal membrane via a prism, and the amount of fluorescence emitted from the excited fluorescent dye is measured with an SPFS detection section.

(Optical System)

The light source used in the assay method of the invention is not particularly limited as long as the light source can cause plasmon excitation in the metal membrane. From the viewpoints of the uniformity in wavelength distribution as well as the intensity of light energy, however, a laser light is preferably used as the light source. It is desirable that the laser light be passed through an optical filter to control the energy and the amount of photons immediately before entering the prism.

The application of laser light causes the generation of surface plasmons on the surface of the metal membrane under attenuated total reflection [ATR] conditions. The surface plasmons provide an electric field enhancement effect to increase the number of photons several tens to several hundreds of times the number of photons in the applied light, thereby exciting the fluorescent dye. The increase in the number of photons by the electric field enhancement effect depends on the refractive index of the transparent support, as well as on the type of metal and the thickness of the metal membrane. In the case of gold, the increase is usually about 10 to 20-fold.

Electrons in the molecules of the fluorescent dye are excited by light absorption and are instantly elevated to the first electron excited state, and then the electrons in this excited state (level) return to the ground state, emitting a fluorescence with a wavelength corresponding to the energy difference.

Examples of the "laser light" include lights from LD with a wavelength of 200 to 900 nm and 0.001 to 1,000 mW, and lights from semiconductor lasers with a wavelength of 230 to 800 nm (the resonance wavelength is determined in accordance with the type of metal used in the metal membrane) and 0.01 to 100 mW.

The "prism" is used to make sure that the laser light having passed through various filters will enter the plasmon excitation sensor efficiently. Preferably, the prism has the same refractive index as the transparent support. In the present invention, various kinds of prisms which allow for setting of total reflection conditions can be selected appropriately. Thus, the angle and the shape of the prism are not particularly limited. For example, a 60° dispersing prism or the like may be used. Examples of the commercially available prisms include the same commercial products as mentioned for the "transparent glass support".

Examples of the "optical filters" include neutral density [ND] filters, polarized filters, cut filters, condenser lenses and diaphragm lenses. A "neutral density [ND] filter" (or a dark filter) is used for the purpose of adjusting the amount of incident laser light. In particular, the use of this filter is preferable in order to ensure high measurement accuracy when the detector used has a narrow dynamic range.

A "polarized filter" is used to polarize the laser light into P polarized light, which generates surface plasmons efficiently.

A "cut filter" eliminates optical noises such as outside light (illumination light from the outside of the apparatus), excitation light (transmitted components of excitation light), stray light (scattered components of excitation light at various points), scattered light of plasmons (scattered light which originates from the excitation light and is caused by the influence of the structure, adherent and the like on the surface of the plasmon excitation sensor), as well as autofluorescence of the fluorescent dye. Examples thereof include interference filters and colored filters.

A "condenser lens" is used in order to condense fluorescent signals to the detector efficiently, and may be any condenser system. It is possible to use a commercially available objective lens (for example, manufactured by Nikon Corporation or OLYMPUS CORPORATION) used in a microscope or the like as a simple condenser system. The magnification of the objective lens is preferably 10× to 100×.

The "SPFS detection section" is preferably a photomultiplier tube [PMT] (a photomultiplier manufactured by Hamamatsu Photonics Co., Ltd.) from the viewpoint of superhigh sensitivity. Further, a CCD image sensor capable of multipoint measurement is also suitable because the fluorescent signals can be viewed as an image and the elimination of noise lights is easy, although the sensitivity is lower compared to a photomultiplier tube.

[Step (e)]

In the step (e), the amount of an analyte contained in the sample is calculated based on the measurement results obtained in the step (d).

In more detail, in the step (e), a calibration curve is prepared by performing measurements with a target antigen or a target antibody having a known concentration, and the amount of the analyte (the target antigen or the target antibody) in the tested sample is calculated from the measured signal based on the calibration curve.

(Analyte)

The "analyte" is molecules or molecular fragments which can be specifically recognized by (or can specifically recognize) the first ligand and bind thereto. Examples of such "molecules" or "molecular fragments" include nucleic acids (such as single stranded or double stranded DNA, RNA, polynucleotides, oligonucleotides and PNA (peptide nucleic acids), as well as nucleosides, nucleotides and modified molecules thereof); proteins (such as polypeptides and oligopeptides); amino acids (including modified amino acids); carbohydrates (such as oligosaccharides, polysaccharides and sugar chains); lipids; and modified molecules and complexes of these molecules. Specific examples include carcinoembryonic antigens and tumor markers such as AFP [a fetoprotein], as well as signal transducers and hormones. However, the "molecules" or "molecular fragments" are not particularly limited to these above.

(Change in Assay Signal)

In the step (e), a change in assay signal can be calculated in accordance with the following equation wherein the "blank signal" is a signal measured before the step (b).

Change in signal=|(Assay fluorescent signal)−(Blank fluorescent signal)|

EXAMPLES

The present invention will be described in detail by presenting examples hereinbelow without limiting the scope of the invention.

Fabrication Example 1

Fabrication of Plasmon Excitation Sensor Used as Sensor Area/Labeled Antibody Purification Area First, a transparent glass support with a refractive index [nd] of 1.72 and a thickness of 1 mm ("S-LAL 10" manufactured by OHARA INC.) was subjected to plasma cleaning. On one surface of the support, a chromium membrane was formed by a sputtering method. Further, a gold membrane was formed on the surface of the chromium membrane by a sputtering method. The thickness of the chromium membrane was 1 to 3 nm, and the thickness of the gold membrane was 44 to 52 nm.

The obtained support was soaked in an ethanol solution containing 1 mM of 11-amino-1-undecanethiol for at least 24 hours, thereby forming a SAM on the surface of the gold membrane. The support was taken out from the solution, washed with ethanol and isopropanol, and thereafter dried with an air gun.

Onto the surface of the support were dropped a 25 mM MES-buffered saline which contained 0.5 mM of N-hydroxysuccinimide [NHS], 0.5 mM of a water-soluble carbodiimide [EDC] and 1 mg/ml of CMD-500-0614 (manufactured by Meito Sangyo Co., Ltd.: average molecular weight: 500,000, substitution degree: 0.51), as well as a 10 mM NaCl solution (pH 6.0), the total volume of the 25 mM MES-buffered saline and the 10 mM NaCl solution being 0.8 mL. After the reaction was carried out for 90 minutes, a 1 N sodium hydroxide solution was fed and the reaction was performed for 30 minutes, thereby immobilizing CMD on the SAM.

Further, onto the surface of the support were dropped a 25 mM MES-buffered saline which contained 100 mM of NHS and 100 mM of EDC, as well as a 10 mM NaCl solution, the total volume of the 25 mM MES-buffered saline and the 10 mM NaCl solution being 0.8 mL. After the reaction was carried out for 20 minutes, 0.8 mL of an MES solution which contained an anti-α-fetoprotein [AFP] monoclonal antibody (1D5: 50 mg/mL, manufactured by Japan Clinical Laboratories, Inc.) was fed and the reaction was performed for 30 minutes. Thus, a primary antibody was immobilized on CMD.

Next, 0.8 mL of a 50 mM Tris (pH 7.4) was allowed to react for 15 minutes so as to block unreacted active ester groups. Further, a reaction was carried out for 30 minutes with a TBS-buffered saline which contained 1% by weight of bovine serum albumin [BSA], thereby performing a non-specific adsorption prevention treatment.

Fabrication Example 2

Fabrication of Sensor Substrate Used as Sample Purification Area

A sensor substrate in which CMD was immobilized on the surface of a support was fabricated in the same manner as in Fabrication Example 1, except that an MES solution containing no anti-α-fetoprotein [AFP] monoclonal antibody (1D5) was used.

Example 1

Implementation of Assay Method Including Steps (a) to (e)

First, the sample purification area formed on the surface of the sensor substrate (Fabrication Example 2) was cleaned three times each with 0.8 mL of a TBS solution which contained 0.05% by weight of Tween 20.

A step (a) was carried out in which 0.8 mL of commercially available bovine serum (manufactured by Kohjin Bio Co., Ltd.) containing 0.1 ng/ml of AFP was brought into contact with the sample purification area for 25 minutes. Thus, CMD-adsorptive components in the bovine serum were removed.

A step (b) was performed in which 0.8 mL of the bovine serum (the sample) obtained from the step (a) was brought into contact with the sensor area formed on the surface of the plasmon excitation sensor (Fabrication Example 1) for 25 minutes.

Next, the sensor area was cleaned three times each with 0.8 mL of a TBS solution which contained 0.05% by weight of Tween 20.

A step (c) was carried out in which 0.8 mL of a secondary antibody (a 1% BSA/PBS solution prepared such that the concentration would be 1 μg/mL) labeled with Alexa Fluor (registered trademark) 647 was added to the sensor area, and the reaction was performed for 20 minutes.

Thereafter, the sensor area was cleaned three times each with 0.8 mL of a TBS solution which contained 0.05% by weight of Tween 20.

A step (d) was performed in which a laser light (633 nm, 10 μW) was applied to the plasmon excitation sensor through the surface of the transparent glass support opposite to the gold membrane via a prism (manufactured by SIGMA KOKI Co., Ltd.), and the amount of fluorescence emitted from the excited fluorescent dye was measured with a photomultiplier tube [PMT]. The measured signal value was obtained as the "assay measurement signal".

Separately, the solution from which the CMD-adsorptive components in the bovine serum had been removed, namely, which contained AFP at 0 ng/mL was tested. The SPFS measurement signal was obtained as the "blank signal".

A step (e) was carried out in which the assay signal was evaluated based on the following equation:

Assay signal=|(Assay measurement signal)−(Blank signal)|

Figure 5:
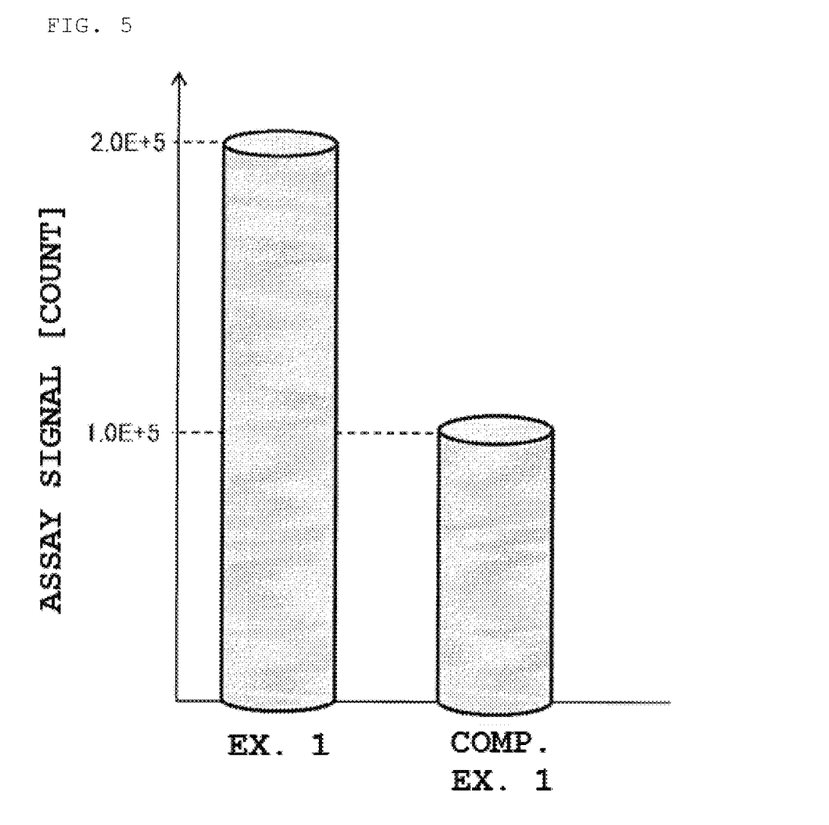
FIG. 5 is a bar graph depicting the assay signals obtained from the results in Example 1 and Comparative Example 1, respectively.

The obtained results are described in FIG. 5.

Example 2

Implementation of Assay Method Including Steps (x) and (a) to (e)

First, the labeled antibody purification area formed on the surface of the plasmon excitation sensor (Fabrication Example 1) was cleaned three times each with 0.8 mL of a TBS solution which contained 0.05% by weight of Tween 20.

A step (x) was carried out in which 0.8 mL of a secondary antibody (a 1% BSA/PBS solution prepared such that the concentration would be 1,000 ng/mL) labeled with Alexa Fluor (registered trademark) 647 was added to the labeled antibody purification area and held in contact therewith for 20 minutes.

The reaction liquid was collected as a purified labeled antibody solution.

An assay method was performed in the same manner as in Example 1, except that a PBS solution which contained 1% by weight of BSA to which 0.1 ng/ml of AFP had been added was used as a sample, and the purified labeled antibody solution was used as a solution containing a secondary antibody.

Figure 6:
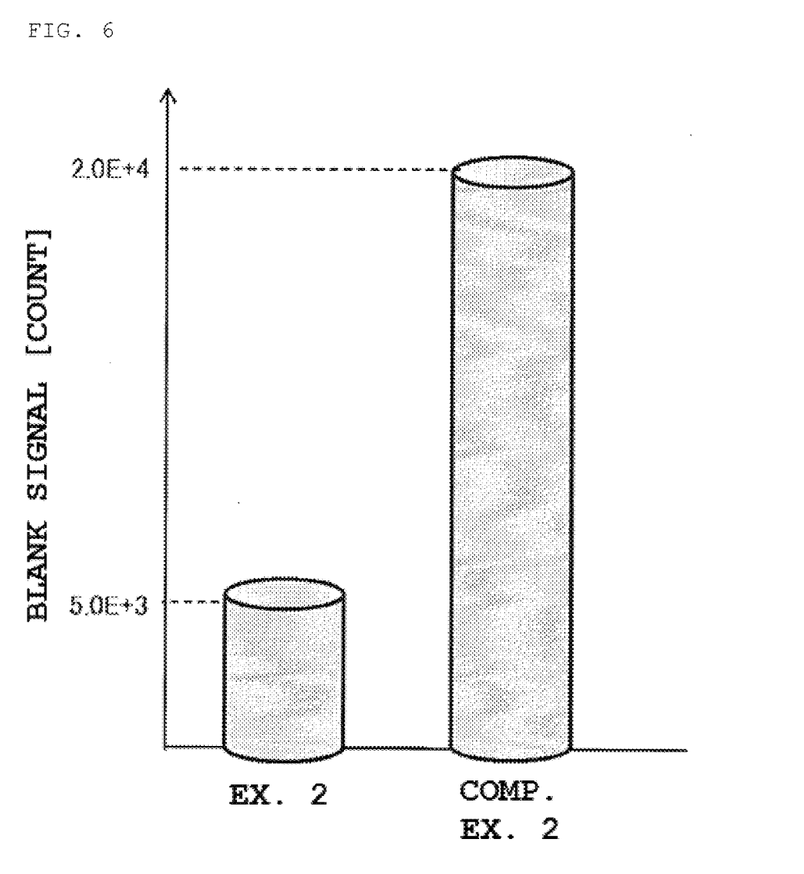
FIG. 6 is a bar graph depicting the blank signals obtained from the results in Example 2 and Comparative Example 2, respectively.

The obtained results are described in FIG. 6.

Comparative Example 1

Implementation of Assay Method without Purification of Sample

An assay method was performed in the same manner as in Example 1, except that the bovine serum was not purified. The obtained results are described in FIG. 5.

Comparative Example 2

Implementation of Assay Method without Purification of Antibody

An assay method was performed in the same manner as in Example 1, except that a PBS solution which contained 1% by weight of BSA to which 0.1 ng/ml of AFP had been added was used as a sample. The obtained results are described in FIG. 6.

INDUSTRIAL APPLICABILITY

The inventive assay method involving a combination of the purification area and the sensor area is capable of detection with high sensitivity and high accuracy. Thus, for example, the inventive assay method can detect even a trace amount of a tumor marker contained in blood, and the obtained results allow for highly accurate estimation of the presence of a non-invasive cancer (intraepithelial carcinoma) at a preclinical stage which cannot be detected by palpation or a similar examination.

The invention claimed is:

1. An SPFS sensor chip, comprising
a purification area and a sensor area arranged upstream and downstream, respectively, relative to each other along a flow direction in a channel for surface plasmon-field enhanced fluorescence spectroscopy [SPFS],
wherein the purification area includes a sample purification area and a labeled antibody purification area,
wherein the channel is in such a form that the sample purification area and the labeled antibody purification area define respective branches and merge with each other to lead to the sensor area, and
wherein the labeled antibody purification area comprises:
a transparent support;
a metal membrane formed on one surface of the transparent support;
a self-assembled monolayer [SAM] formed on the surface of the metal membrane opposite to the transparent support;
a hydrophilic polymer layer formed on the surface of the SAM opposite to the metal membrane; and
a bioactive substance immobilized on the surface of the hydrophilic polymer layer opposite to the SAM.

2. The SPFS sensor chip according to claim 1, wherein the sensor area comprises:
a transparent support;
a metal membrane formed on one surface of the transparent support;

a self-assembled monolayer [SAM] formed on the surface of the metal membrane opposite to the transparent support;

a hydrophilic polymer layer formed on the surface of the SAM opposite to the metal membrane; and a bioactive substance immobilized on the surface of the hydrophilic polymer layer opposite to the SAM.

3. The SPFS sensor chip according to claim 1, wherein the purification area comprises:

a transparent support;

a metal membrane formed on one surface of the transparent support;

a self-assembled monolayer [SAM] formed on the surface of the metal membrane opposite to the transparent support; and a hydrophilic polymer layer formed on the surface of the SAM opposite to the metal membrane; and the sensor area comprises:

a transparent support;

a metal membrane formed on one surface of the transparent support;

a SAM formed on the surface of the metal membrane opposite to the transparent support;

a hydrophilic polymer layer formed on the surface of the SAM opposite to the metal membrane; and a bioactive substance immobilized on the surface of the hydrophilic polymer layer opposite to the SAM; and further wherein a hydrophilic polymer forming the purification area layer in the sensor substrate, and a hydrophilic polymer forming the sensor area in the plasmon excitation sensor are different from each other.

4. The SPFS sensor chip according to claim 1, wherein the purification area is arranged in the entirety of a channel portion upstream from the sensor area.

5. An SPFS sensor chip, comprising a purification area and a sensor area arranged upstream and downstream, respectively, relative to each other along a flow direction in a channel for surface plasmon-field enhanced fluorescence spectroscopy [SPFS], wherein the purification area comprises a sample purification area and a labeled antibody purification area, wherein the channel is in such a form that the sample purification area and the labeled antibody purification area define respective branches and merge with each other to lead to the sensor area, and wherein the sample purification area comprises a transparent support;

a metal membrane formed on one surface of the transparent support;

a self-assembled monolayer [SAM] formed on the surface of the metal membrane opposite to the transparent support; and a hydrophilic polymer layer formed on the surface of the SAM opposite to the metal membrane.

6. The SPFS sensor chip according to claim 2, wherein the bioactive substance in the labeled antibody purification area is the same as the bioactive substance in the sensor area.

* * * * *